United States Patent [19]
Ju et al.

[11] Patent Number: 5,599,325
[45] Date of Patent: *Feb. 4, 1997

[54] THIN WALL CATHETER WITH REINFORCING SLEEVE

[75] Inventors: Byung H. Ju, Golden Valley; Michael G. O'Connor, Blaine; Eric M. Lovgren, Buffalo, all of Minn.

[73] Assignee: Schneider (USA) Inc, Plymouth, Minn.

[*] Notice: The term of this patent shall not extend beyond the expiration date of Pat. No. 5,403,292.

[21] Appl. No.: 350,779

[22] Filed: Dec. 7, 1994

Related U.S. Application Data

[63] Continuation-in-part of Ser. No. 245,428, May 18, 1994, Pat. No. 5,403,292.

[51] Int. Cl.⁶ .................................................. A61M 25/00
[52] U.S. Cl. ........................... 604/282; 604/264; 128/658
[58] Field of Search .................................... 604/282, 280, 604/264, 265, 51; 128/656–658

[56] References Cited

U.S. PATENT DOCUMENTS

| | | | |
|---|---|---|---|
| 4,563,181 | 1/1986 | Wijayarathna et al. | 604/280 |
| 4,898,591 | 2/1990 | Jang et al. | 604/282 |
| 5,221,270 | 6/1993 | Parker | 604/282 |
| 5,226,899 | 7/1993 | Lee et al. | 604/282 |
| 5,254,107 | 10/1993 | Soltesz | 604/282 |
| 5,318,032 | 6/1994 | Lonsbury et al. | 128/658 |
| 5,403,292 | 4/1995 | Ju | 604/282 |

FOREIGN PATENT DOCUMENTS

| | | |
|---|---|---|
| 0117093A3 | 8/1984 | European Pat. Off. . |
| 0420486A1 | 4/1991 | European Pat. Off. . |
| 0520692A1 | 12/1992 | European Pat. Off. . |
| 0555088A2 | 8/1993 | European Pat. Off. . |
| 0566755A1 | 10/1993 | European Pat. Off. . |
| 9001345 | 2/1990 | WIPO . |
| 9002579 | 3/1990 | WIPO . |

*Primary Examiner*—John D. Yasko
*Attorney, Agent, or Firm*—Peter C. Richardson; Lawrence C. Akers; Philip C. Strassburger

[57] ABSTRACT

A diagnostic catheter comprises an inner layer of substantially unmodified polyamide over which is a reinforcing means and an outer layer of polymer having a hardness of 50 Shore D to 70 Shore D, along with a suitable radiopaque filler. Affixed either directly to the end of the above tubular body or to a stem member secured to that tubular body is a soft-tip formed from a blend of PEBA whose hardness is such that the catheter can be considered as having an atraumatic tip. The resulting catheter exhibits excellent torque and column strength characteristics while providing a relatively large diameter lumen for a given outside diameter.

20 Claims, 3 Drawing Sheets

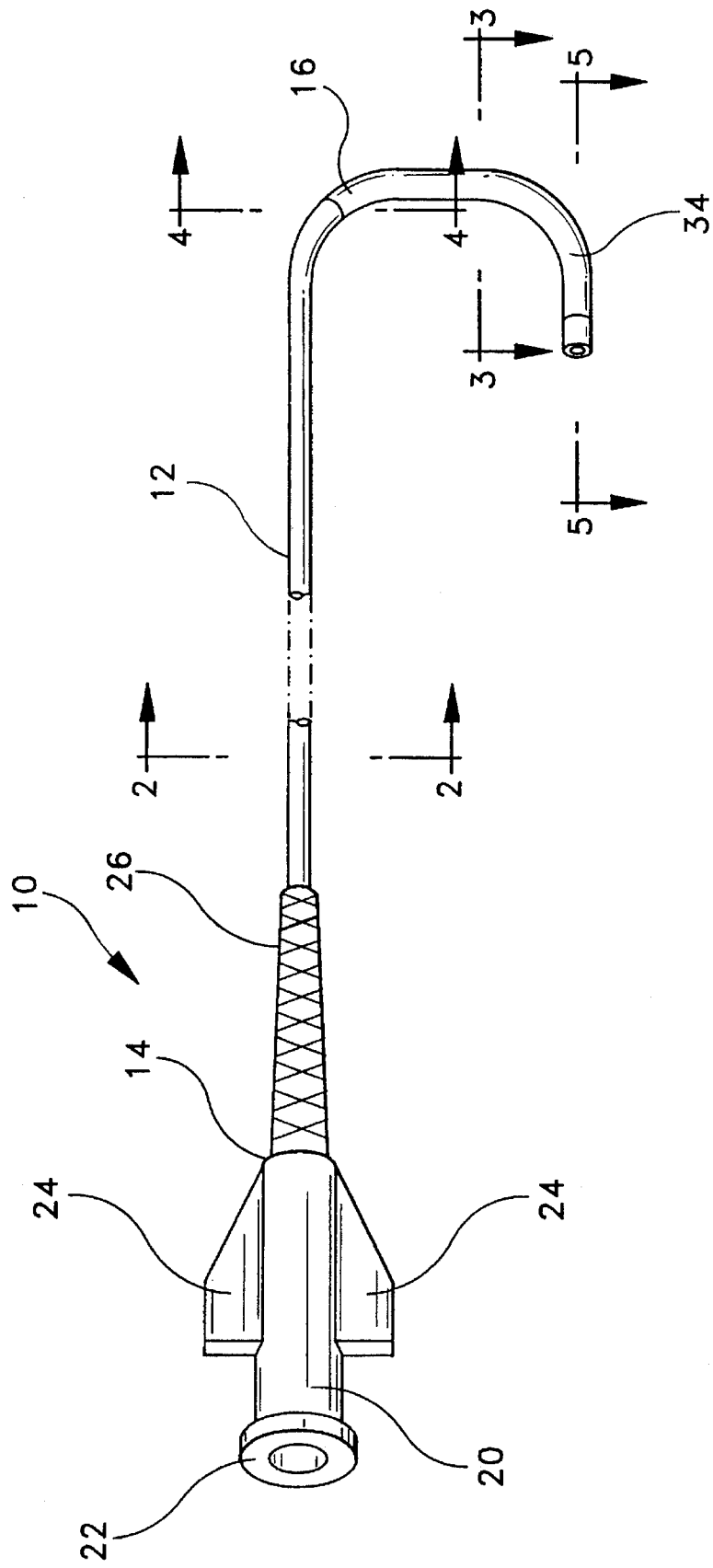

THIN WALL CATHETER WITH REINFORCING SLEEVE

This patent application is a continuation-in-part of U.S. patent application Ser. No. 08/245,428, filed May 18, 1994 now U.S. Pat. No. 5,403,292.

BACKGROUND OF THE INVENTION

The present invention relates to intravascular catheters, and more particularly to a diagnostic catheter having a relatively small outside diameter for its relatively large diameter internal lumen and which possesses excellent pushability and torqueability characteristics.

In evaluating the progress of coronary artery disease in patients, angiography procedures are used to view the patency of selected blood vessels. In carrying out this procedure, a diagnostic catheter having a desired distal end curvature configuration is introduced into the femoral artery using the Seldinger technique and advanced over a guide wire through the vascular system of the patient until the distal end of the catheter is steered into the particular coronary artery to be examined. With smaller patients, a brachial or radial approach may be used.

In that the path taken by the diagnostic catheter is quite tortuous, it is essential to a good diagnostic catheter that it can be steered by torquing its proximal hub and that the torque be transmitted to the distal end in a smooth, controllable fashion. Moreover, the catheter must have sufficient strength in the longitudinal direction so as not to kink or fold as it is advanced through the vascular system. It must also possess a lubricous core lumen to facilitate passage of a guidewire or possibly another catheter therethrough.

It is also a desirable feature of a diagnostic catheter that it possess a relatively large lumen to allow fluids, such as radiopaque contrast fluid to be injected therethrough and out the distal end so that the area of the vascular system under investigation can be viewed fluoroscopically.

The desirable properties of a catheter having a relatively small O.D. and a relatively large I.D. dictates a fairly thin wall. To maintain the desired torqueability and pushability characteristics of a thin wall catheter calls for considerable ingenuity in the formulation of the materials employed and the constructional techniques utilized.

The Jang et al. U.S. Pat. No. 4,898,591 describes a diagnostic catheter having a tubular body formed from inner and outer tubular layers, there being a strengthening braid interposed between the inner and outer layers. The inner layer is formed from a blend of a nylon and an ester-linked polyether-polyamide copolymer.

The present invention is an advance over the prior art as represented by the Jang et al. patent in that it provides a diagnostic catheter having a minimal O.D. and a maximal I.D. while still maintaining the necessary torqueability and pushability characteristics. Using the method and the constituents for the various layers set forth herein, it has been possible to design a diagnostic catheter having, for example, a 4 Fr O.D. but with an internal lumen that is as large as the internal lumen of a 5 Fr catheter that is currently commercially available. Similarly, a 6 Fr catheter made in accordance with the present invention possesses an internal lumen that is about equal to that of a commercially-available 7 Fr catheter.

SUMMARY OF THE INVENTION

In accordance with the present invention there is provided a diagnostic intravascular catheter having an elongated tubular body with a proximal end, a distal end and a lumen extending therebetween where the tubular body is formed with an inner layer consisting essentially of an unmodified polyamide polymer, preferably Nylon-12. As used herein, the term "unmodified polyamide polymer" refers to the fact that nothing is added to the polymer matrix that tends to substantially change its physical properties, such as copolymers, polymer blends, miscible polymers in relation to polyamide-based polymer matrices or polymer performance enhancers which would substantially change the physical properties of the polymer. For instance, the fact that a colorant or a radiopaque filler material is added is not considered to be a modification. The fact that a small amount of an ester-linked polyether-polyamide copolymer is blended with the polyamide polymer is not considered to be a modification if it does not substantially change the physical properties.

Nylon is hydrophobic meaning that it does not absorb moisture and swell. Surrounding the inner layer is a reinforcing means. The reinforcing means may comprise braided filaments and may constrict the inner layer, creating microscopic bumps on the wall surface defining the lumen, effectively decreasing the contact area between an inserted guidewire and the wall surface. The reinforcing means may alternatively consist of a perforated metal tube, a perforated plastic tube, plastic mesh, or plastic fabric.

An outer layer, including a polymer having a predetermined durometer hardness in the range of from about 50 Shore D to about 75 Shore D and preferably a radiopaque filler material ($BASO_4$), covers the inner layer and the reinforcing means. It can provide an outer diameter to the tubular body in the range of from 3–8 Fr.

Preferably affixed to the distal end of the tubular body member is a soft-tip member, which may be molded from a blend of resins such that the soft tip exhibits a hardness that is less than about 45 Shore D.

The intravascular catheter may also incorporate a non-braided tubular stem member that is interposed between and bonded to both the tubular body and the soft-tip member. The stem member itself preferably comprises a single layer of a copolymer of polyamide and PEBA whose Shore hardness is in the range of from 25 D to 72 D. It may have a uniform or tapered outer diameter.

In sum, the present invention relates to an intravascular catheter having an elongated tubular body with a proximal end, a distal end and a lumen extending therebetween. The tubular body has (a) an inner layer consisting essentially of an unmodified polyamide polymer; (b) a reinforcing means at least partially surrounding the inner layer; and (c) an outer polymeric layer having a predetermined durometer hardness in the range of from about 50 Shore D to about 75 Shore D, the outer layer at least partially covering said reinforcing means. The intravascular catheter can further include an annular soft-tip member bonded to the distal end of the tubular body member, and the soft-tip member can be a blend of resins having a hardness less than about 45, Shore D. A tubular stem member may be interposed between and bonded to both the tubular body and the soft-tip member, the stem member being a copolymer of a polyamide and a polyether block amide, said copolymer having a Shore hardness in the range of from about 25 D to 72 D. The inner layer may be a 100 percent polyamide polymer. The inner layer may have a wall thickness in the range of from about 0.001 to 0.008 inches (0.0025 to 0.0203 cm), preferably about 0.0025 inches (0.0064 cm). The reinforcing means may be totally embedded between the inner layer and outer layer. The outer layer may further comprise a radiopaque filler material. The stem member may include a radiopaque filler material. The tubular body and the tubular stem may have the same outer diameter. The tubular stem member may be tapered from a first outside diameter equal to the outside diameter of the tubular body at a junction between the tubular body and the tubular stem member to a lesser diameter. The outer layer may be a blend of Nylon-12 polyamide, polyether block amide, and a radiopaque filler. The lumen may have a diameter in the range of from about 0.026 to 0.080 inch (0.066 to 0.203 cm) and the outer layer may have an outer diameter in the range of from about 0.039 to 0.110 inch (0.099 to 0.279 cm). The blend may be 19.3% by weight polyamide, 44.5% by weight PEBA, 36% by weight $BaSO_4$ radiopaque filler and 0.2% by weight of a pigment. The outer layer may include a polyether block amide (PEBA) of a predetermined hardness in the range of from about 50 Shore to 75 Shore D. The outer layer may be a blend of 63.8% by weight 72 D PEBA, 36% by weight $BaSO_4$ radiopaque filler and 0.2% by weight of a pigment. The reinforcing means may be a braided metal sleeve configuration of filaments and said sleeve may extend from said proximal portion of the tubular body toward the distal portion of the tubular body by a predetermined distance. Alternatively, the reinforcing means may be a perforated metal tube, or it may be a polymer forming a mesh, a tube, or a fabric.

When attempts are made to thermally bond a soft-tip or a stem member to a braid-reinforced tubular body, the cut free ends of the wires comprising the braid may distort due to heat and penetrate through the heat-softened wall of the tubular body either into the lumen or through the outer wall. To obviate this problem, the catheter of the present invention generally incorporates a ring or band formed from a suitable metal or from a high temperature resistant plastic, such as polyimide sold under the trademark, KAPTON. This thin ring captures the ends of the wires comprising the braid, preventing them from fraying or otherwise distorting as a thermal bonding of a soft-tip or a tubular stem member takes place.

DESCRIPTION OF THE DRAWINGS

The foregoing features, objects and advantages of the invention will become apparent to those skilled in the art from the following detailed description of a preferred embodiment, especially when considered in conjunction with the accompanying drawings in which like numerals in the several views refer to corresponding parts. These figures are provided to illustrate, and not limit, the present invention.

FIG. 1 is a perspective view of a diagnostic catheter constructed in accordance with the present invention;

DESCRIPTION OF THE PREFERRED EMBODIMENT

Figure 4:
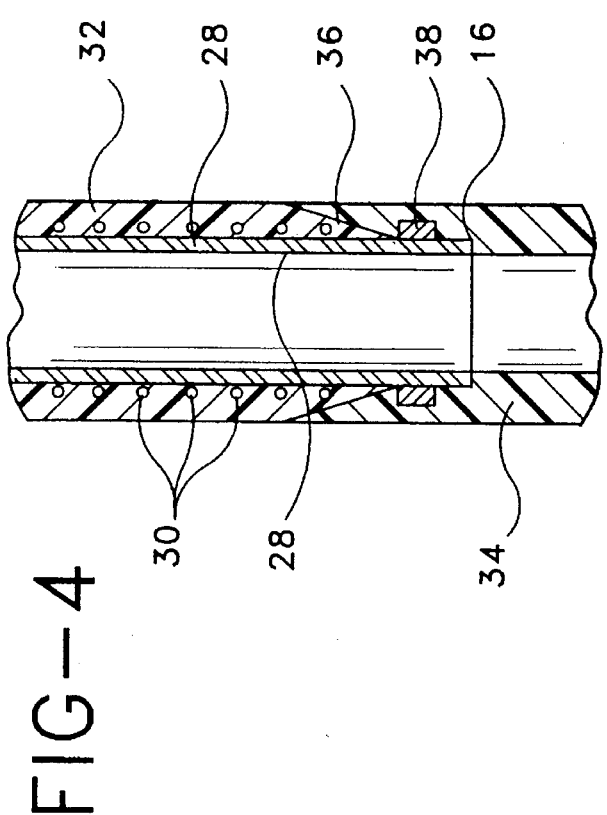
FIG. 4 is a longitudinal cross-sectional view taken along the line 4—4 which passes through the joint between the tubular body stock and the stem member.
Figure 5:
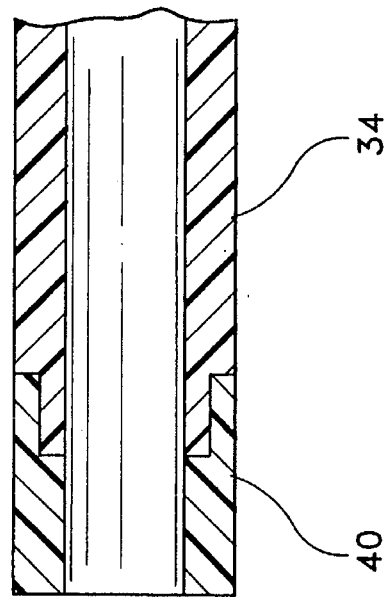
FIG. 5 is a longitudinal cross-sectional view taken through the distal end portion of the catheter along the line 5—5 in FIG. 1.

Referring first to FIG. 1, there is indicated generally by numeral 10 a diagnostic catheter comprising the present invention. It includes an elongated tubular body 12 having a proximal end 14, a distal end 16 and a lumen 18 extending therebetween. Affixed to the proximal end 14 of the tubular body 12 is a molded plastic hub 20 having a Luer fitting 22 at its proximal end and flared wings 24 projecting radially from the diametrically opposed sides thereof to facilitate twisting of the catheter. An elastomeric sleeve 26 surrounds the proximal end portion of the tubular body 12 and functions as a strain relief member. The sleeve 26 is preferably toughened or knurled to facilitate gripping and rotation thereof using a three-finger catheter engagement. The length of the tubular body 12 will typically be 3½ to 4 feet in length and will have an outside diameter that is generally uniform over this length and will come in various sizes from, say, 3 Fr to 8 Fr.

Figure 2:
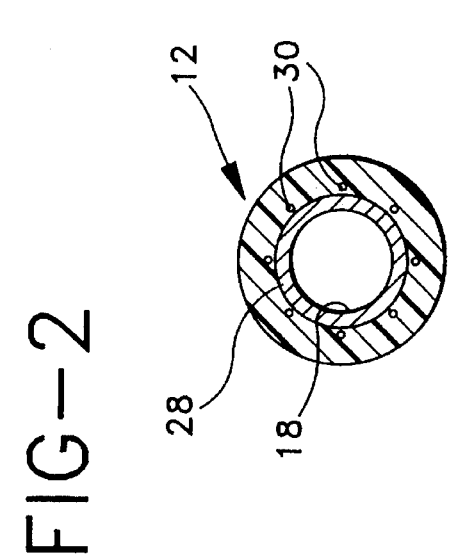
FIG. 2 is a cross-sectional view of the catheter of FIG. 1 taken along the line 2—2.
Figure 3:
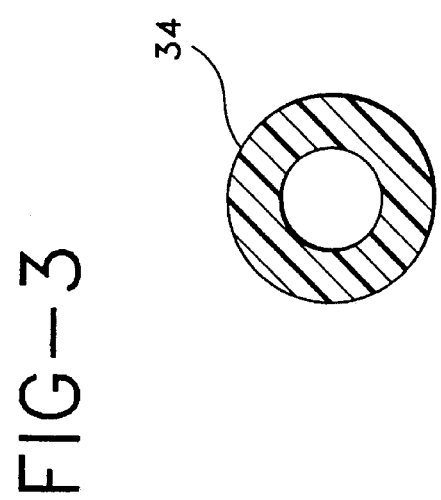
FIG. 3 is a cross-sectional view taken through the stem member of the catheter along the line 3—3 in FIG. 1.

Referring to the cross-sectional view of FIG. 2, it can be seen that the tubular body 12 is formed with an inner layer 28 which is preferably an unmodified polyamide, such as Nylon-12®. With this polyamide as the material for the inner layer 28, the surface defining the lumen 18 is inherently lubricous. Moreover, Nylon-12 is found not to absorb moisture and, hence, will not change in dimension when immersed in saline, body fluids and/or contrast media liquid. The inner layer 12 preferably has a wall thickness in the range of from about 0.001 to 0.008 inch (0.0025 to 0.0203 cm) with 0.0025±0.0005 inch (0.0064±0.0013 cm) being preferred.

As can also be seen in the cross-sectional views of FIGS. 2 and 4, a reinforcing means, in this case a braided sleeve of metal wires 30 is formed about the inner layer 28. More particularly, the inner layer 28 will typically be extruded over a polyacetal mandrel, and following extrusion, is braided using stainless steel braid wire. Any one of a number of braid patterns may be used including, without limitation, staggered 2-over-2-under or staggered 1-over-1-under. The braid angle may be adjusted to range anywhere from 20° to 60° from the perpendicular plane of the catheter. Again, without limitation, the braid wire diameter may fall in the range of from 0.0010 to 0.0030 inches. As the wires are braided about the central inner layer 28, minor deformations occur at the point of contact between the braid wires and the Nylon-12 inner layer, creating tiny irregularities in the surface of the lumen 18. It is found that these irregularities reduce the effective wall contact area between, say, a guidewire or an angioplasty catheter that might be inserted through the lumen, thereby reducing friction still further than is provided by the lubricous nature of the Nylon-12 material itself.

Figure 6:
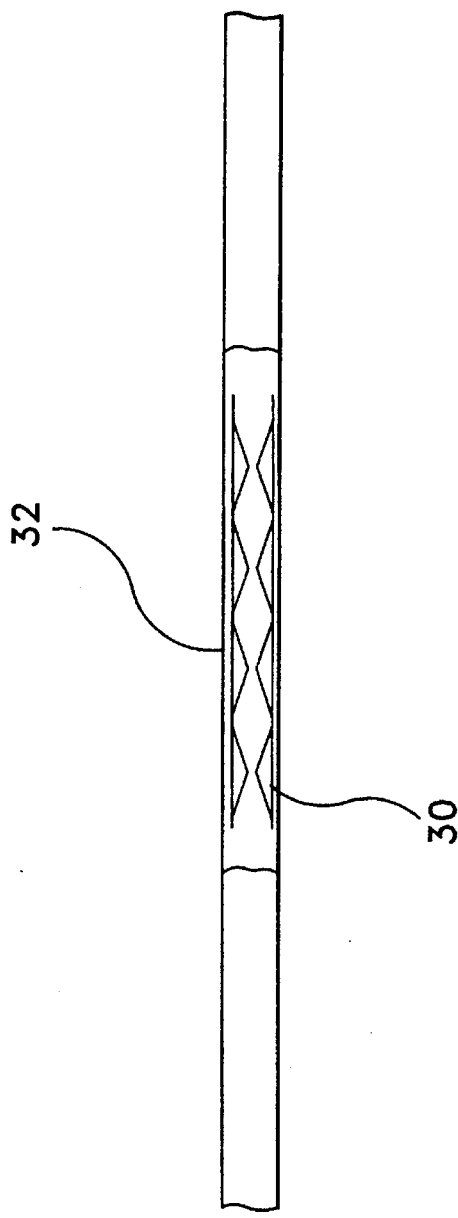
FIG. 6 is a cross-sectional view of a catheter having a perforated metal tube as a reinforcing means.
Figure 7:
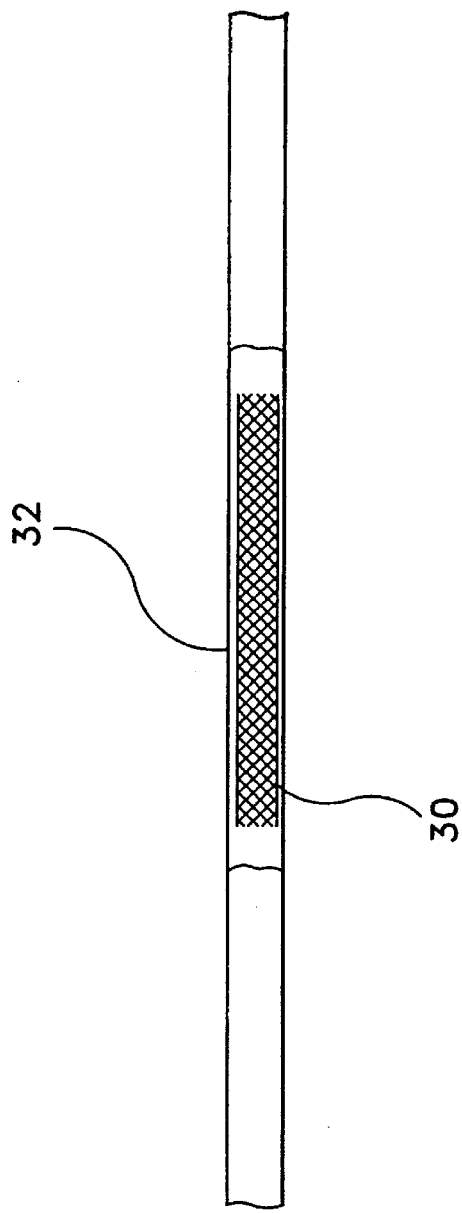
FIG. 7 is a cross-sectional view of a catheter having a plastic mesh as a reinforcing means.

Alternative reinforcing means include a perforated metal tube, a perforated plastic tube, a plastic mesh, a contiguous plastic tube, and a plastic fabric. If a perforated tube is used, the tube may have perforations or slots of various shapes, such as ovals, circles, rectangles, or triangles with or without beveled edges. Methods of forming openings in metal tubes are disclosed in Kraus et al. (U.S. Pat. No. 5,256,144); and Samson et al. (U.S. Pat. No. 4,998,923). (All documents cited herein, including the foregoing, are incorporated herein by reference in their entireties for all purposes.) A plastic tube, plastic mesh and/or plastic fabric may comprise polymers such as polycarbonate, polyurethane, and polyethylene. FIG. 6 shows a catheter having a perforated metal tube as a reinforcing means 30, and FIG. 7 shows a plastic mesh as a reinforcing means 30. Metal tubes may be made of a shape memory alloy.

Following placement of the reinforcing means, an outer layer 32 is extruded onto the assembly. The outer layer may comprise polyether block amide (PEBA) of a predetermined durometer hardness in the range from about 50 Shore D to 75 Shore D and preferably contains a radiopaque filler, such as barium sulfate $BaSO_4$. As can be seen from the cross-sectional views of FIGS. 2 and 4, the outer layer 32 totally embeds the reinforcing means 30 and the die used with the extruder will provide a predetermined wall thickness yielding an outer diameter to the tubular body that is selected to be anywhere in the range of from 3 Fr to 8 Fr.

While the inner layer 28 of the catheter is preferably formed from 100% Nylon-12 polyamide, the outer layer may comprise polymers such as a blend of polyether block amides that exhibit differing durometers to yield a catheter body having a desired stiffness characteristic or "feel". The outer layer 32 may also be a blend of polyamide and PEBA. Thus, for example, the outer layer may be a blend including, say, 63.8% by weight of a 72 D PEBA having 36% $BaSO_4$ added as a radiopaque filler and 0.2% by weight of a pigment to provide a desired color to the tubular body. As another example, the outer layer may comprise a blend of 19.3% by weight polyamide, 44.5% of 70 D PEBA and 36% by weight of $BaSO_4$ again with 0.2% by weight of a pigment added for color.

To provide a desired shape characteristic to the distal end portion of the diagnostic catheter, a tubular stem member 34 is thermally bonded to the distal end portion of the braided tubular body 12. As is best seen in FIG. 4, the braided tubular body has its outer layer or jacket 32 ground to a bevel as at 36. By beveling the distal end portion 16 of the tubular body 12, greater surface area is provided for effecting attachment of the stem member 34. In that the grinding operation used to create the bevel reduces the thickness of the outer jacket relative to the ends of the wires 30 comprising the braided sleeve, it has been found expedient to provide a band or ring 38 of a non-penetrable material surrounding the free ends of the braid wires. Without such a band, the heating required to effect a thermal bond between the tubular body 12 and the jacket 34 can cause the frayed ends of the braid to warp or bend to the point where they can penetrate through the inner layer 28 into the lumen 18 or through the thickness of the tubular stem 34. The band 38 confines those ends during heating, preventing such undesired wall penetration. With no limitation intended, the band of non-penetrable material may comprise a metal, such as tantalum, titanium, iridium, gold, silver, stainless steel and alloys of such materials. Alternatively, a suitable high temperature polymers, such as polyimide, e.g., KAPTON, can be used to constrain the free ends of the braid wires from penetrating the interior or exterior wall of the catheter during thermal bonding re-flow procedures.

The stem member 34 will preferably comprise a blend of PEBA ranging from, say, 25 D to 72 D with a polyamide, such as Nylon-12, along with a radiopaque filler, e.g., barium sulfate, being added, along with a desired pigment.

Preferred amounts of barium sulfate are 0–36 weight percent for the inner layer; 0–42 weight percent for the outer layer; and 0–42 weight percent for the stem. Additional materials may be included, such as pigments in the amounts of from 0.001–0.5 weight percent for the inner layer; 0.001–0.5 weight percent for the outer layer; and 0.001–0.5 weight percent for the stem. Additional materials that may be added include titanium dioxide, bismuth sub carbonate and iodine compounds.

Completing the catheter is a soft-tip member 40 which may be bonded to the distal end portion of the stem member 34. In forming the soft-tip on the catheter, a suitable low durometer (25 D–40 D) PEBA can be used. Alternatively, a PEBA blend with 15% to 45% by weight of radiopaque filler, such as $BaSO_4$, may be used. In particular, a resin blend consisting of 48.6% 25 D PEBA, 32.4% 40 D PEBA, 15% $BaSO_4$ and 4% $TiO_2$ pigment has been found to provide a soft, atraumatic tip. That tip may be formed by injection molding the material onto the distal end of the stem member 34. Alternatively, if the catheter is not designed to include a stem member, the soft-tip 40 may be injection molded directly onto a distal end portion of the braided tubular body 12 with a impenetrable ring 38 again being used to confine the braiding wire ends as the soft tip is being formed.

Using the above techniques, it has been possible to produce a 3 Fr O.D. catheter having a lumen with a diameter of 0.026 inches and which still possesses excellent torquing characteristics whereby the distal end of the catheter follows a rotation of its proximal end. Moreover, even with such a relatively large diameter lumen in comparison to its outer diameter, the catheter still has adequate column strength allowing it to be advanced through the vascular system without kinking or buckling. An 8 Fr diagnostic catheter constructed in accordance with the present invention may have a lumen as large as 0.076 inches, again having the desirable properties expected by most cardiologists as far as its ability to be manipulated through the application of longitudinal and rotational forces at the proximal end portion of the catheter.

Those skilled in the art will also appreciate that the intravascular catheter in accordance with the present invention can be manufactured to have a variety of different distal end shaped configurations to suit the desires of different cardiologists.

Various modifications and changes in detail may be made to the above-described embodiments and examples without departing from the spirit and scope of the invention. It is therefore intended that all such matter as described and shown in the attached drawings and in the foregoing description be considered as illustrative only and not limiting.

What is claimed is:

1. An intravascular catheter comprising:
   an elongated tubular body having a proximal end, a distal end and a lumen extending therebetween, the tubular body comprising:
   (a) an inner layer consisting essentially of an unmodified polyamide polymer;
   (b) a reinforcing means at least partially surrounding the inner layer;
   (c) an outer polymeric layer having a predetermined durometer hardness in the range of from about 50 Shore D to about 75 Shore D, the outer layer at least partially covering said reinforcing means;
   (d) an annular soft-tip member bonded to the distal end of the tubular body member; and
   (e) a tubular stem member interposed between and bonded to both the tubular body and the soft-tip member, the stem being a copolymer having a Shore hardness in the range of from about 25 D to 72 D.

2. The intravascular catheter of claim 1 and wherein the soft-tip member comprises a blend of resins and has a hardness less than about 45 Shore D.

3. The intravascular catheter of claim 2 wherein the stem member is a copolymer of a polyamide and a polyether block amide.

4. The intravascular catheter of claim 1 wherein the inner layer is of a 100 percent polyamide polymer.

5. The intravascular catheter of claim 4 wherein the inner layer has a wall thickness in the range of from about 0.001 to 0.008 inches (0.0025 to 0.0203 cm).

6. The intravascular catheter of claim 5 wherein the wall thickness is about 0.0025 inches (0.0064 cm).

7. The intravascular catheter of claim 1 wherein the reinforcing means is totally embedded between the inner layer and outer layer.

8. The intravascular catheter of claim 1 wherein the outer layer further comprises a radiopaque filler material.

9. The intravascular catheter of claim 3 wherein the stem member includes a radiopaque filler material.

10. The intravascular catheter of claim 3 wherein the tubular body and the tubular stem have the same outer diameter.

11. The intravascular catheter of claim 3 wherein the tubular stem member is tapered from a first outside diameter equal to the outside diameter of the tubular body at a junction between the tubular body and the tubular stem member to a lesser diameter.

12. The intravascular catheter of claim 1 wherein the lumen is of a diameter in the range of from about 0.026 to 0.080 inch (0.066 to 0.203 cm) and the outer layer has an outer diameter in the range of from about 0.039 to 0.110 inch (0.099 to 0.279 cm).

13. The intravascular catheter of claim 12 wherein the lumen is of a diameter in the range of from about 0.026 to 0.080 inch (0.066 to 0.203 cm) and the outer layer has an outer diameter in the range of from about 0.039 to 0.110 inch (0.099 to 0.279 cm).

14. The intravascular catheter of claim 12 wherein the blend comprises 19.3% by weight polyamide, 44.5% by weight PEBA, 36% by weight $BaSO_4$ radiopaque filler and 0.2% by weight of a pigment.

15. The intravascular catheter of claim 1 wherein the outer layer includes a polyether block amide (PEBA) of a predetermined hardness in the range of from about 50 Shore to 75 Shore D.

16. The intravascular catheter of claim 1 wherein the outer layer is a blend comprising 63.8% by weight 72 D PEBA, 36% by weight $BaSO_4$ radiopaque filler and 0.2% by weight of a pigment.

17. The intravascular catheter of claim 1 wherein said reinforcing means is a braided metal sleeve configuration of filaments and said sleeve extends from said proximal portion of the tubular body toward the distal portion of the tubular body by a predetermined distance.

18. The intravascular catheter of claim 1 wherein said reinforcing means is a perforated metal tube or a metal tube made of a shape memory alloy.

19. The intravascular catheter of claim 1 wherein said reinforcing means comprises a polymer forming a mesh, a tube, or a fabric.

20. An intravascular catheter comprising:
   an elongated tubular body having a proximal end, a distal end and a lumen extending therebetween, the tubular body comprising:
   (a) an inner layer consisting essentially of an unmodified polyamide polymer;
   (b) a reinforcing means at least partially surrounding the inner layer; and
   (c) an outer polymeric layer comprising a blend of Nylon-12 polyamide, polyether block amide, and a radiopaque filler, the blend having a predetermined durometer hardness in the range of from about 50 Shore D to about 75 Shore D, the outer layer at least partially covering said reinforcing means.

* * * * *